(12) United States Patent
Shpantzer (10) Patent No.: US 7,502,118 B2
(45) Date of Patent: *Mar. 10, 2009

(54) HIGH SENSITIVITY COHERENT PHOTOTHERMAL INTERFEROMETRIC SYSTEM AND METHOD FOR CHEMICAL DETECTION

(75) Inventor: Isaac Shpantzer, Bethesda, MD (US)

(73) Assignee: CeLight, Inc., Silver Spring, MD (US)

( * ) Notice: Subject to any disclaimer, the term of this patent is extended or adjusted under 35 U.S.C. 154(b) by 140 days.

This patent is subject to a terminal disclaimer.

(21) Appl. No.: 11/677,185

(22) Filed: Feb. 21, 2007

(65) Prior Publication Data

US 2007/0127030 A1 Jun. 7, 2007

Related U.S. Application Data

(63) Continuation-in-part of application No. 11/672,372, filed on Feb. 7, 2007, and a continuation-in-part of application No. 11/561,966, filed on Nov. 21, 2006, now Pat. No. 7,426,035, and a continuation-in-part of application No. 10/947,640, filed on Jan. 13, 2005, now Pat. No. 7,277,178, and a continuation-in-part of application No. 10/669,130, filed on Sep. 22, 2003, now Pat. No. 7,327,913.

(51) Int. Cl.
G01B 9/02 (2006.01)
G01J 3/45 (2006.01)

(52) U.S. Cl. .................................... 356/451
(58) Field of Classification Search ................ 356/128, 356/432, 451, 484, 517
See application file for complete search history.

(56) References Cited

U.S. PATENT DOCUMENTS

| 4,943,709 A | * | 7/1990 | Grinberg et al. | ......... 250/201.9 |
| 5,060,312 A | * | 10/1991 | Delavaux | .................... 398/204 |
| 5,699,464 A | * | 12/1997 | Marcuse et al. | ............... 385/33 |
| 6,709,857 B2 | * | 3/2004 | Bachur, Jr. | ............... 435/288.7 |

(Continued)

OTHER PUBLICATIONS

"Fiber coupling with adaptive optics for free space optical communications" by Weyrauch et al., Proceedings SPIE, 2002, v. 4489, p. 177-183.

(Continued)

*Primary Examiner*—Michael A Lyons
(74) *Attorney, Agent, or Firm*—Nadejda Reingand

(57) ABSTRACT

A photo-thermal interferometric spectroscopy system is disclosed that provides information about a chemical at a remote location. A first light source assembly is included that emits a first beam. The first beam has one or more wavelengths that interact with the chemical and change a refractive index of the chemical. A second laser produces a second beam. The second beam interacts with the chemical resulting in a third beam with a phase change that corresponds with the change of the refractive index of the chemical. A detector system is positioned remote from the chemical to receive at least a portion of the third beam. An adaptive optics system at least partially compensates the light beam degradation caused by atmospheric turbulence. A focusing system is used to bring together the light passed through the chemical; the focusing system includes a multimode fiber for the light collection, The detector system provides information on a phase change in the third beam relative to the second beam that is indicative of at least one of, absorption spectrum and concentration of the chemical.

20 Claims, 8 Drawing Sheets

(a)

(b)

U.S. PATENT DOCUMENTS

| | | | |
|---|---|---|---|
| 7,277,178 B2 * | 10/2007 | Shpantzer et al. | 356/451 |
| 2003/0067657 A1 | 4/2003 | Dimmler | |
| 2004/0086282 A1 | 5/2004 | Graves | |
| 2006/0024061 A1 | 2/2006 | Wirth | |

OTHER PUBLICATIONS

Stephen E. Bialkowski entitled "Photothermal Spectroscopy Methods for Chemical Analysis", John Wiley & Sons, Inc., 1996, pp. 331-337.

* cited by examiner (a)

HIGH SENSITIVITY COHERENT PHOTOTHERMAL INTERFEROMETRIC SYSTEM AND METHOD FOR CHEMICAL DETECTION

CROSS-REFERENCE TO RELATED APPLICATIONS

This application is a continuation-in-part of U.S. Ser. No. 10/947,640 filed Jan. 13, 2005 now U.S. Pat. No. 7,277,178 and Ser. No. 11/561,966 filed Nov. 21, 2006 now U.S. Pat. No. 7,426,035, both of which applications are fully incorporated herein by reference. This application is a continuation-in-part of U.S. Ser. No. 10/669/130 filed Sep. 22, 2003 now U.S. Pat. No. 7,327,913 and Ser. No. 11/672,372 filed Feb. 7, 2007.

FIELD OF INVENTION

This invention relates generally to systems and methods for chemical detection such as explosives and others, and more particularly to photothermal interferometric spectroscopy devices, and their methods of use, based on optical signal detection.

BACKGROUND OF THE INVENTION

The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein. Photothermal spectroscopy method allows carrying out extremely sensitive measurements of optical absorption in homogeneous media. It is possible, using, a laser's coherent and powerful output, to obtain extremely sensitive measurements of optical absorption that exceed those of mass spectroscopy by two or three times, and produce accurate results from only a few molecules.

Co-pending U.S. patent application Pub. No. 20050105099 by the same inventor as the present application discloses implementation of coherent receiving technique for photothermal interferometric sensing. Integrated 90-degrees optical hybrid is a key component of the coherent receiver, This method provides improved sensitivity of the detection.

Laser free-space propagation is effected by atmospheric conditions such as turbulence and the like which works to cause aberrations in the spatial phase of the wavefront of the laser beams. The beam spreading and scintillation induced by the atmospheric turbulence cannot be compensated by increasing of optical power because of eye safety and power consumption. A considerable improvement is achieved by implementing adaptive optics systems such as described, for example, in U.S. Patent applications Nos. 20040086282 filed Oct. 16, 2003 by Graves (FIG. 4) and 20060024061 filed Feb. 2, 2006 by Wirth (See FIG. 3) and a number of publications, see for example, "Fiber coupling with adaptive optics for free space optical communications" by Weyrauch et al., Proceedings SPIE. 2002, v. 4489, p. 177-183, all of which incorporated herein by references.

In "Fiber coupling with adaptive optics for free space optical communications" by Weyrauch et al., Proceedings SPIE, 2002, v. 4489, p. 177-183 the laser beam coupling in multimode and single mode fiber is demonstrated. Obviously implementation of multimode fiber provides a number of advantages. First of all, larger sensitivity of the light beam detection is achieved because the diameter of multimode fiber is about 10 times larger than the diameter of single mode fiber. Secondly, the tolerance to the optical beam misalignment is attained since the diameter of multimode fiber is much larger than the focal spot size of a beam with uniform intensity distribution, while the focal spot size is compatible with a mode-field diameter of single-mode fiber.

There is a need for remote methods and systems for detecting for the presence of chemicals in the field which provide improved sensitivity due to elimination of atmospheric turbulence effects and improved coupling efficiency at the receiver.

SUMMARY OF THE INVENTION

Accordingly, an object of the present invention is to provide improved remote methods and systems directed to chemical detection, such as explosives and the like, where the detector system is positioned at a remote location. The preset invention addresses methods and systems directed to chemical sensing that include adaptive optics system to compensate atmospheric turbulence in a light beam passing through the chemical.

Yet another object of the present invention is to provide improved remote methods and systems directed to chemical sensing that implement a multimode fiber for collection of the light passed through the chemical.

Another object of the present invention is to provide photothermal interferometric spectroscopy devices, and their methods of use, for the remote detection of chemical, and the like.

These and other objects of the present invention are achieved in, a photothermal, interferometric spectroscopy system that provides information about a chemical at a remote location. A first light source assembly is included that emits a first beam. The first beam has one or more wavelengths that interact with the chemical and change a refractive index of the chemical. A second laser produces a second beam. The second beam interacts with the chemical resulting in a third beam with a phase change that corresponds with the change of the refractive index of the chemical. A detector system is positioned remote from the chemical to receive at least a portion of the third beam. An adaptive optics system is positioned to compensate the atmospheric turbulence effects in the light beam. The detector system provides information on a phase change in the third beam relative to the second beam that is indicative of at least one of, absorption spectrum and concentration of the chemical. A multimode fiber is used to collect light that passed through the chemical. A single mode fiber is used to insert this light in a waveguide of the integrated part of the detector system.

In another embodiment of the present invention, a method is provided for determining information about a chemical at a remote location. A first beam is directed to a remote location where a chemical is present. The first beam has one or more wavelengths that interact with the chemical and changes a refractive index of the chemical. A second beam is directed to the chemical and interacts with the chemical to form a third beam. The third beam has a phase change relative to the second beam that corresponds with a change of a refractive index of the chemical. At least a portion of the third beam is passed through adaptive optics system and received at a detection system positioned remote from the chemical. A phase shift of the third beam is measured that is induced by the first beam and is indicative of at least, one of, absorption spectrum and concentration of the chemical. The third beam is collected by a multimode fiber, then coupled to a single mode fiber and inserted in a coherent receiver. A phase shift of the third beam is measured that is induced by the first beam and is indicative of at least, one of, absorption spectrum and concentration of the chemical.

BRIEF DESCRIPTION OF THE DRAWINGS

FIG. 1 is a block diagram of a photothermal interferometric spectroscopy system of the present invention that has a temporal referenced beam: (a) with reflected probe beam, (b) with transmitted probe beam.

DETAILED DESCRIPTION OF THE PREFERRED EMBODIMENT

Co-pending U.S. Patent application Publ. No. 20050105099 discloses an optical device which is a part of the block diagram shown in FIG. 1(a), where 10 is a unit that combines strobe generation and targeting, 11 is the unit for optical probe beam generation and targeting, 12 is a signal detection and recovery block, and 13 is electronics control and processing block. The system operates as follows: the strobe laser 14 feeds integrated wideband $Li_2NbO_3$ Optical Comb Generator 15. The comb generator 15 enables the programming and launching of very short pulses (pico-seconds) that are pre-shaped in the frequency domain to match the absorption spectra of the substance under study, such as explosives or another. In the preferred embodiment the pre-shaped strobe is fed to one of the non-linear ZnSe optical mixer 16 while its other input is coupled with the Optical Parametric Oscillator (OPO) 17. The output of the mixer 16 results in strobe-spectra at the applicable absorption region of the interrogated chemical substance in the wavelength range of 0.2-20 micron. The strobe beam (this beam is called "the first beam" in the present invention) is directed by targeting unit 18 to a specific location inside the examined chemical volume 19 by preferably a MEMs steering mechanism. The chemical under study is also illuminated by a probe beam (this beam is called "the second beam") or a set of beams 20 coming from the light source 21 and passing the targeting unit 22. In the preferred embodiment of the present invention, shown in FIG. 1(a), the probe set of beams 23 passed the interrogated chemical is reflected by the reflection surface 24. Collecting optics 25 collects the part of reflected light (this beam is called "the third beam") and forwards it to coherent detector 26 that includes 90-degrees optical hybrid. A local oscillator 26a provides a reference signal to the coherent detector 26. The electrical output signal 27 from the coherent detector is processed in DSP unit 28. Digital synthesizer and control unit 29 controls DSP unit 28, optical parametric oscillator 17, laser 14 and optical comb generator 15.

Figure 1:
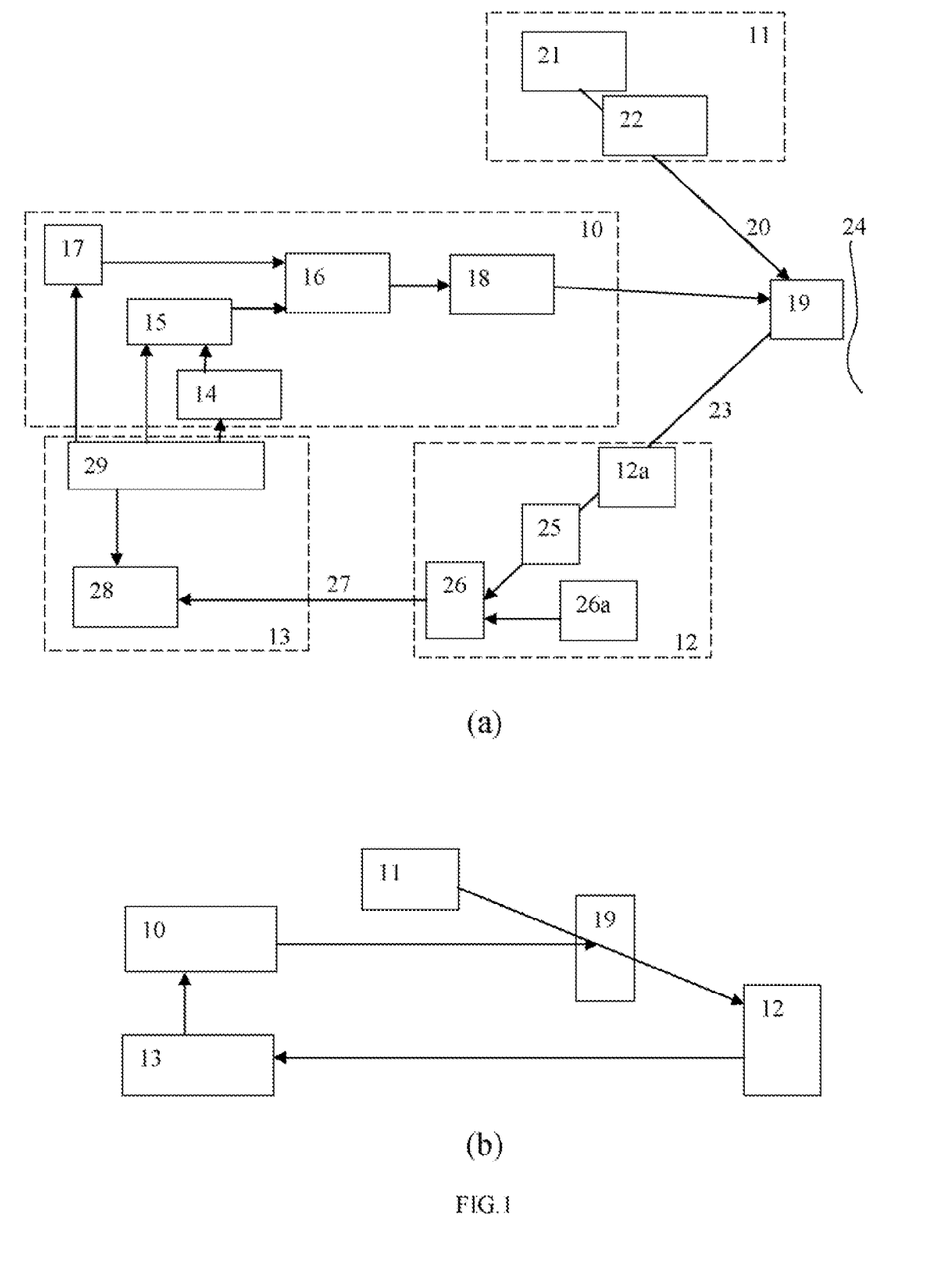

The system of the present invention additionally includes adaptive optics system 12a positioned in the receiving unit 12.

Another embodiment of the present invention is a system operating without the background reflection surface. The background surface can be eliminated if there is enough back scattered light in the interrogated chemical volume to carry out the detection.

FIG. 1(b) shows this embodiment of the present invention. This is the analogous scheme for the chemicals detection but operating in the transmission mode. In certain situations it could be possible to install the light transmitter 11 and detector 12 on the opposite sides of the interrogated chemical volume 19. This allows the chemical detecting without background reflection surface. The adaptive optics system is a part of the detector 12.

The detected molecules can be brought into the excited state from which it relaxed by the following processes: (i) direct one-photon absorption; (ii) two-photons absorption and (iii) two-photons stimulated Raman process. The stimulated Raman process enables the use of less exotic light sources that simplify and optimize the overall system.

In the preferred embodiment the light of two orthogonal polarizations is used for the chemical illumination to provide complete information for data recovery.

Probing of the interrogated chemical is performed by one of two methods:

(1) Temporal referenced method,
(2) Spatial referenced method.

Temporal Referenced Method

Figure 2:
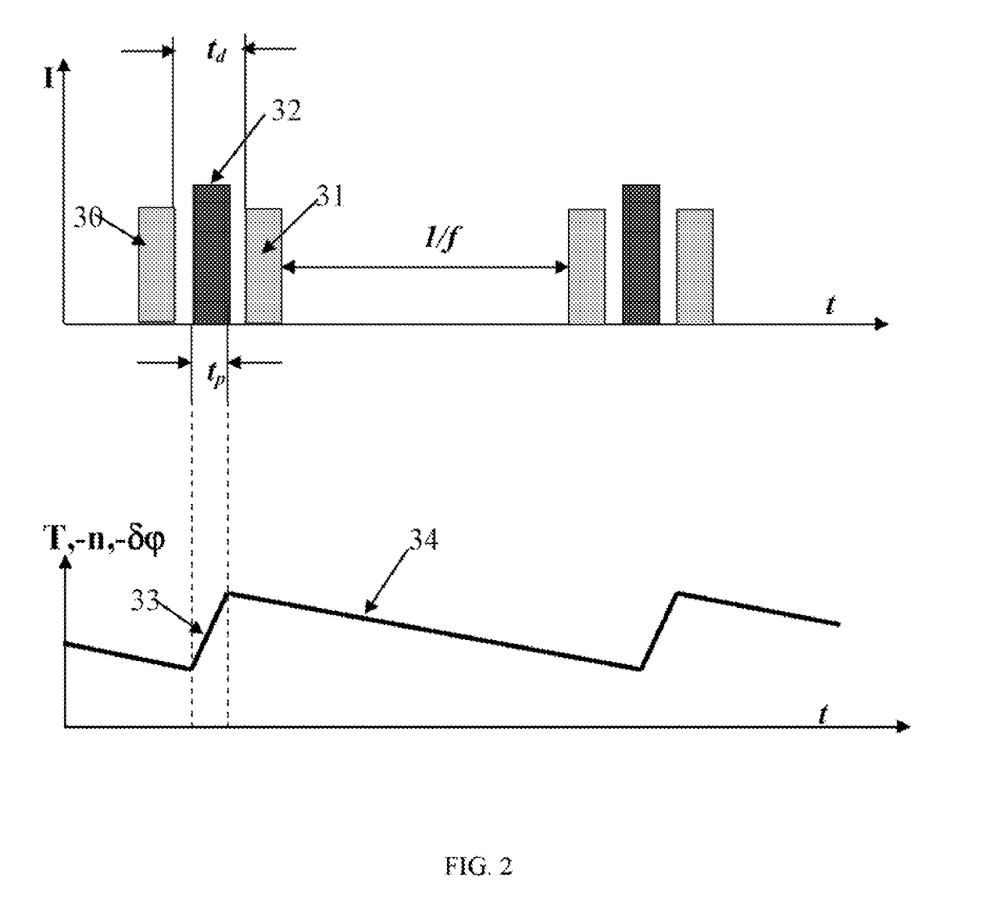
FIG. 2 illustrates a change of the refractive index of interrogated chemical and time location of the strobe and probe pulses in the case of a pair pulses probe beam in one embodiment of the present invention.

The probe pulse (FIG. 2) is split in to two and recombined into a two-pulse sequence 30 and 31, separated by a time $t_d \geq t_p$ where $t_p$ is the duration of strobe pulse 32. The resulting sequence of pulses in shown in FIG. 2. The lower part of the figure shows the rapid change of the refractive index 33 in interrogated media followed by relaxation 34. The phase delay will be measured by interfering the probe signal with its time delay version using the balanced detector. Major advantage lies in the fact that if the time delay $t_d$ is short, the atmospheric noise and vibration noise are not existent. The calculations below show that the minimum detectable concentration is $10^{-10}$ cm$^{-1}$ that is better than 1 ppb.

Figure 3:
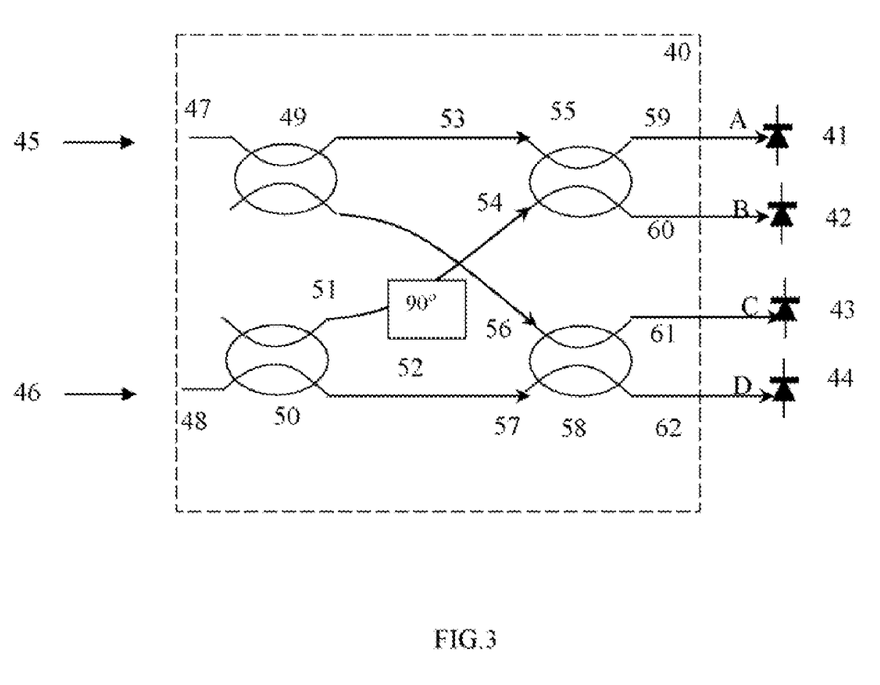
FIG. 3 is a schematic diagram of a balanced detector of the present invention with 90-degrees optical hybrid.

The interrogated chemical temperature experiences a rapid rise that leads to the rapid change of the refractive the index that causes a phase delay in the probe beam. The phase delay is measured by interfering the probe signal with its time delay version using the balanced detector. The schematic diagram of the balanced detector is shown in FIG. 3. It consists of a 90-degrees optical hybrid 40 and four balanced photodetectors 41-44. Two incoming optical signals 45 and 46, called, respectively the signal S and the local oscillator L, impinge two inputs 47 and 48 of the optical hybrid. Both signal beam S and local oscillator L beam are divided by the first set of 3 dB couplers 49 and 50 as shown in FIG. 3. The beam 51 passes through the phase shifter 52 and gains the additional phase shift of 90 degrees. The beams 53 and 54 are combined together at the directional coupler 55. Respectively, the beams 56 and 57 are combined together at the directional coupler 59. The resulting four output signals A, B, C, D coming, respectively, from the outputs 59, 60, 61 and 62, all having 90-degrees relative phase difference of the form: A=S+L, B=S−L, C=S+jL and D=S−jL.

In the preferred embodiment the balanced detector is used as described in the U.S. patent applications Publ. Nos.

20040096143 and Ser. No. 11/672,372 by the same inventor incorporated herein by reference.

Figure 4:
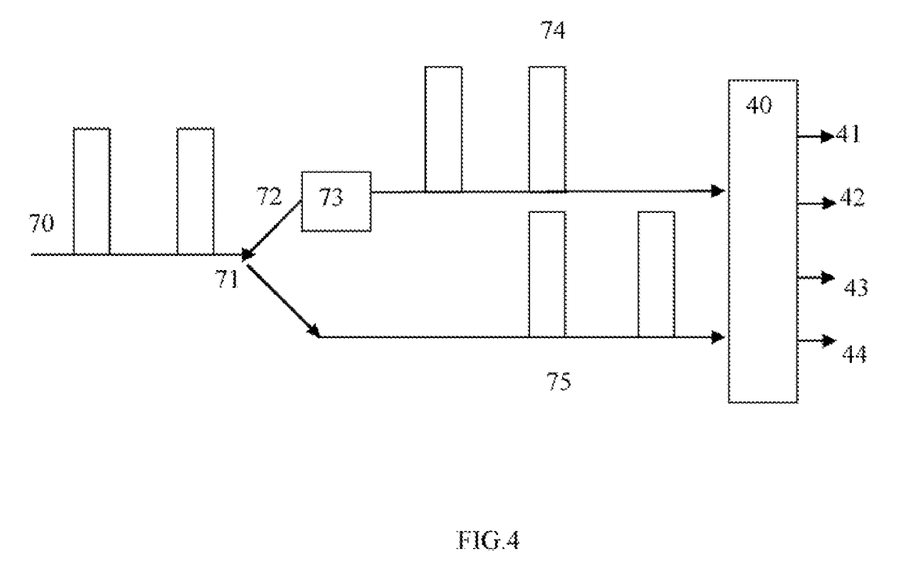
FIG. 4 illustrates interference of the pulse with the delayed pulse on the detector from FIG. 3.

FIG. 4 shows one embodiment of data recovery. Two signals, one of which is time delayed, are overlapping at the detector. Incoming signal 70 is splitted at splitter 71, and the beam 72 experiences the delay at the delay line 73. The delay time is chosen to be the same as a time delay between two pulses in the pair. As the result of this delaying of one of the beams, the pulses 74 and 75 impinge the coherent detector at the same time. Since the pulse 74 corresponds to the heated chemical, and pulse 75 is the reference pulse, the information of the phase change in the laser beam due to the refractive index change can be recovered after detection.

Figure 5:
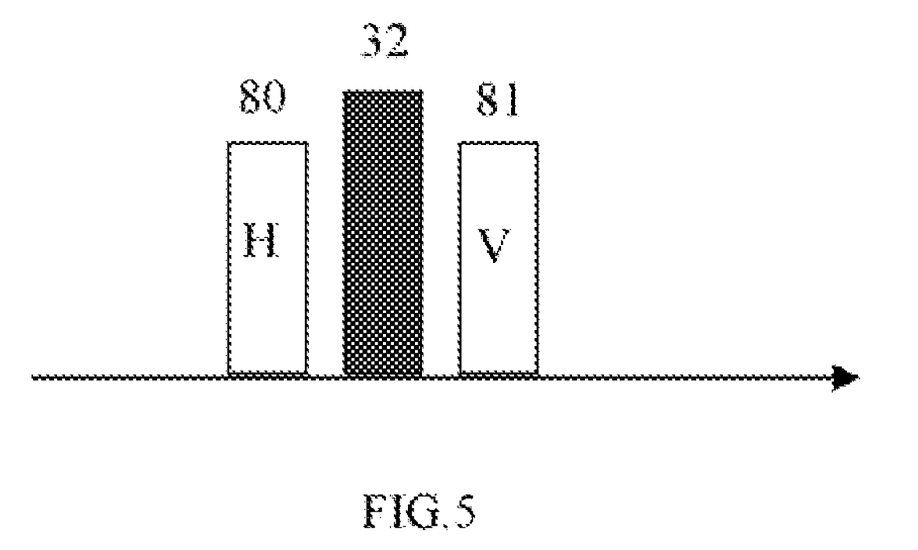
FIG. 5 illustrates a polarization multiplexed pair of pulses in one embodiment of the present invention.

Another embodiment uses polarization multiplexed configuration of probe pulses as shown in FIG. 5 in order to eliminate the delay line at the receiver. Pulse 80 and pulse 81 have orthogonal polarization states (H and V). There are various techniques to implement such polarization multiplexed dual-pulse probe laser. To help elucidate the principle an example of one such implementation is described next.

Figure 6:
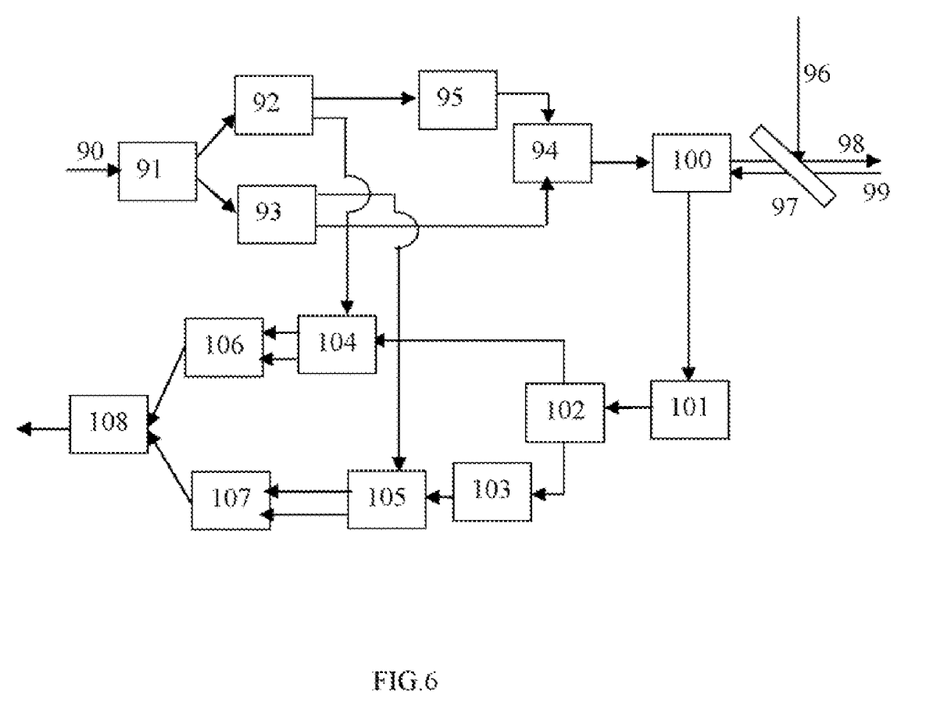
FIG. 6 illustrates polarization multiplexed signal generation and detection setup in one embodiment of the present invention.

The dual-pulse probe laser can be constructed by polarization multiplexing using a configuration shown in the FIG. 6. The input probe pulse train 90 at the far left is divided into four paths using polarization maintaining or PM fiber-optic couplers (PMCs) 91, 92 and 93. The probe pulses in two of the obtained PM optical fibers are combined orthogonally using a polarization beam combiner (PBC) 94. The two PM fibers have a relative length difference introduced by a delay line 95. It corresponds to a relative time delay, $\tau$, which is the temporal separation of the two neighboring probe pulses. The output of the PBC is a probe pulse train with two orthogonally polarized neighboring pulses (V and H) with the H-polarized pulse delayed by $\tau$ relatively to the V-polarized pulse as shown in the FIG. 5.

Strobe pulses 96 reflected from the semitransparent mirror 97 heats up the interrogated chemical. The strobe 96 and probe 98 pulse trains are assumed to be synchronized as shown in FIG. 5.

The returned probe pulse train 99 is directed to the receiver through a circulator 100 as shown in the FIG. 6. A polarization controller 101 followed by a polarization beam splitter (PBS) 102 are used to separate the two orthogonal polarized probe pulses (V and H) into two separate optical PM fibers. The two PM fibers have a relative length difference introduced by the delay line 103. The length difference corresponds to a relative time delay, $\tau$, similar to above but the V-polarized pulse is delayed so that the two pulses are aligned to overlap in time. The two probe pulses are combined with the two local oscillator (LO) pulses at 90-degrees optical hybrids 104 and 105 before impinging balanced detectors 106 and 107 as shown in the figure. The two outputs of the balanced detectors are then subtracted from each other at 108 in order to cancel out the common-path phase noise experienced by both V- and H-polarized probe pulses. The subtraction can also be performed digitally after passing the outputs of the balanced detectors to analog-to-digital converters. With digital signal processing compensation of the relative time delay of the two signals can be performed digitally thereby eliminating, the fiber delay line at the receiver.

It was shown that sensitivity of the coherent detection is in order of magnitude higher than the sensitivity of direct detection, see U.S. Patent application 20050105099 by the same inventor as the present invention.

The further improvement of the sensitivity can be achieved by increasing the light collection efficiency $\gamma$ since the sensi tivity is proportional to $\gamma$. The sensitivity of the coherent detection is the following.

$$SNR_{INT} \approx \frac{\eta_2 \gamma_2}{h\nu_2} f \Delta t A^2 Q_1^2 Q_2 \left[ \frac{n-1}{\lambda_2 w^2 kT} \right]^2$$

Here index 1 refers to the strobe and index 2 to the probe, $\eta$ is the detector's quantum efficiency, w is the strobe beam radius, k is the specific heat, Q is the pulse energy, $\Delta$ is the time of measurement. The time delay $t_d$ is short that eliminates the atmospheric and vibration noises.

In the preferred embodiment 10 mJ pulses at required decent repetition rate are obtained using regenerative amplifiers produced by Positive Light, Santa, Clara, Calif.

The estimated minimal detectable concentration is the following. We define the minimum change of absorption that we can detect as $A_{min} = \alpha_{min} L$, where $\alpha$ is absorption coefficient and L is the length of focus of the strobe laser or the size of outgasing cloud whichever is smaller.

$$A_{min} \sqrt{\frac{h\nu_2}{\eta_2 \gamma_2 (f \Delta t) Q_2}} \frac{\lambda_2 w^2 kT}{(n-1)Q_1}$$

The minimum detectable concentration is about $10^{-10}$ cm$^{-1}$; this is better than 1 ppb.

Further reduction of the minimum detectable concentration can be achieved by increasing the light collection efficiency $\gamma$, since it is proportional to $$\frac{1}{\sqrt{\gamma}}.$$

Figure 7:
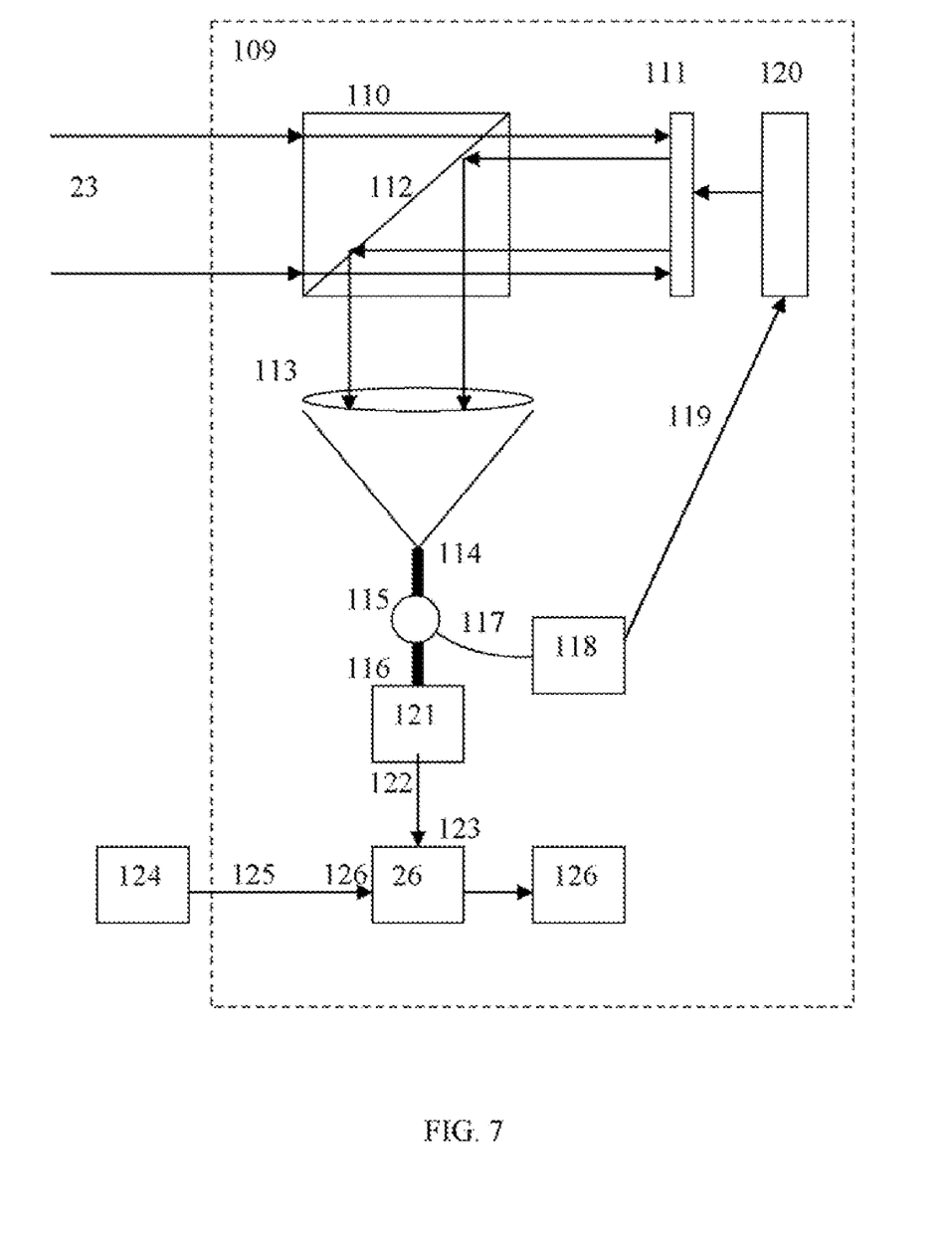
FIG. 7 is a schematic diagram of the detector system with an adaptive optics system and a multimode fiber used to collect light that passed through the chemical.

FIG. 7 shows one of the embodiments of the coherent optical receiver with increased light collection efficiency.

The light beam 23 with the phase change that corresponds to the heating of the interrogated volume impinges receiving unit 109. The part of the beam 23 that passes a beam splitter 110 without reflection impinges adaptive optics (AO) element 111, which can be a deformable mirror. After reflection from the AO element 111 and semi-reflecting plane 112 of the splitter 110, the light beam is focused by a focusing element 113 into a fiber 114. Splitter 115 splits the light beam in the fiber into two directions 116 and 117. The fiber 117 is connected to a sensor 118 which outputs signal 119 being fed in a controller 120 that controls the adaptive optics element 111. The fiber 116 is connected to the coherent optical receiver 26. In the preferred embodiment the fibers 114 and 116 are multimode fibers and the receiver 26 is an integrated receiver as disclosed in co-pending U.S. patent application Ser. No. 11/672,372 filed Feb. 7, 2007 by the same inventor. A multimode-to-single-mode coupler 121 is used to insert light from the multimode fiber to a single mode fiber 122 which is connected to the input 123 of the receiver 26. A local oscillator light source 124 outputs a light beam 125 which enters another input 126 of the receiver 26. The receiver 26 is connected to the digital processing unit (DSP) 126 where the data about the phase change is recovered. The phase change is indicative of at least one of, absorption spectrum and concentration of the chemical.

U.S. Pat. No. 5,699,464 discloses a multimode-to-singemode coupler that may be used as the element 121.

The adaptive optics coupling system includes the splitter 115 connected the sensor 118 providing input to the controller 120 that controls the adaptive optics element 111. Such system was proposed in "Fiber coupling with adaptive optics for free space optical communications" by Weyrauch et al., Proceedings SPIE, 2002, v. 4489, p. 177-183, which incorporated herein by references.

A schematic diagram to obtain a high power tuneable light strobe source covering whole mid-IR range was described in details in the parent application U.S. Publ. No. 20050105099.

Spatial Referenced Method

Figure 8:
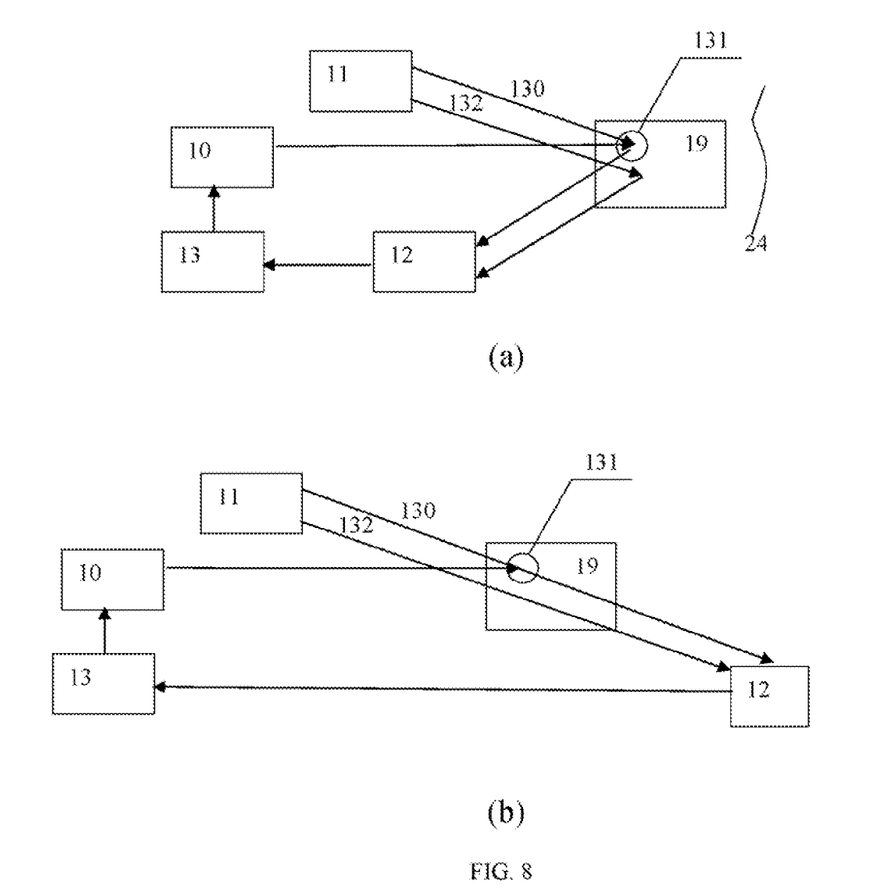
FIG. 8 is a block diagram of a photothermal interferometric spectroscopy system with a spatial referenced beam in one embodiment of the present invention.

In one embodiment of the present invention, two or more probe beams are used, and they are focused on certain distance inside and near the chemical volume under study as shown in FIGS. 8(a) and (b) for reflection-type and transmission-type sensing (two beams case is shown). The probe beams generation and targeting unit 11 outputs two beams, which are slightly spatially resolved. One probe beam 130 is focused in the location of the strobe laser focus 131, and the reference probe beam 132 is focused out of the area of the strobe laser influence. After reflection from the reflective surface 24 (FIG. 8a) two probe beams impinge the coherent detector 12. The change of phase of the first probe beam relatively to another one is recovered followed by DSP processing 13. In the preferred embodiment the coherent detector is used as described in the U.S. patent application Publ. No. 20040096143 "Optical coherent detector and optical communications system and method" by the same invention incorporated herein by reference. The information on the interrogated chemical concentration is recovered. Since the coherent detection is used the of this system is higher (similar to time reference system) compared to the standard system described in S. E. Bialkowski Photothermal Spectroscopy Methods for Chemical Analysis, John Wiley & Sons, Inc., 1996, incorporated herein by reference.

FIG. 8b discloses a similar schematics for chemical detection using spatial reference signal, but operating in a transmission mode. The detector 12 collects light passed through the chemical under study 19.

Experimental results on Remote Gas Detection Using Photothermal Interferometric Spectroscopy are disclosed in the parent U.S. Patent application Publ. No. 20050105099 filed Jan. 13, 2005 by the same inventor, incorporated herein by reference.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A photo-thermal interferometric spectroscopy system that provides information about a chemical at a remote location, comprising: a light detector system positioned remote from the chemical, the detector system having two inputs: a first input receiving a light signal from a local oscillator and a second input receiving a light beam passed through the chemical, an adaptive optics unit to at least partially compensate the light beam degradation caused by atmospheric turbulence in the light beam passed through the chemical, wherein the detector system includes a digital signal processing unit to recover information about at least one of absorption spectrum and concentration of the chemical.

2. The system of claim 1, wherein the adaptive optics unit is a deformable mirror.

3. The system of claim 1, further comprising: a focusing unit to focus the light beam into the second input.

4. The system of claim 1, further comprising: a coherent receiver being a part of the light detector system, the coherent receiver including a 90-degrees optical hybrid connected to at least two balanced photodetectors.

5. The system of claim 4, further comprising: a multimode fiber connected to the second input.

6. The system of claim 4 further comprising: a single mode fiber connected to the multimode fiber and a coupler to insert the light beam from the multimode fiber to the single mode fiber, the single mode fiber being connected to the coherent receiver.

7. The system of claim 1, wherein the chemical is in the form of a gas, liquid or solid.

8. The system of claim 1, wherein the chemical is at an explosive site, a site of pollution and a site of a chemical weapon.

9. The system of claim 1, wherein the remote location is selected from, an explosive standoff location, outside of a blast range, inside a blast range, and at an entry point.

10. The system of claim 1, wherein the detector system is positioned at least 1-1000 meters from the chemical.

11. The optical system of claim 1, wherein the detector system provides homodyne detection of the light beam passed through the chemical.

12. The system of claim 1, wherein the detector detects a plurality of chemicals at one time.

13. The system of claim 1, further comprising a first light source assembly that emits a first beam, the first beam having one or more wavelengths that interact with the chemical and change a refractive index of the chemical; a second laser that produces a second beam, the second beam interacting with the chemical.

14. The system of claim 13, wherein the first light source beam generates a spectrum of wavelengths in at least one of the near, mid and far infrared ranges.

15. The system of claim 14, wherein the mid IR wavelengths are 2.5-20 micron.

16. The optical system of claim 13, wherein the second light source is a pulsed light source.

17. The optical system of claim 13, wherein the first light source is a pulsed light source.

18. A method for determining information about a chemical at a remote location, comprising:
compensating atmospheric turbulence effects in a light beam passed through the chemical,
receiving at least a portion of the light beam passed through the chemical, mixing the portion of the light beam with a local oscillator beam in a coherent receiver;
measuring a phase shift of the light beam, the phase shift being indicative of at least one of absorption spectrum and concentration of the chemical.

19. The method of the claim 18, further comprising: focusing the light beam passed through the chemical into a multimode fiber, coupling the multimode fiber into a single mode fiber, and connecting the single mode fiber to a detector system input.

20. The method of the claim 18, further comprising: directing a first beam to a remote location where a chemical is present, the first beam having one or more wavelengths that interact with the chemical and changing a refractive index of the chemical; directing a second beam to interact with the chemical.

* * * * *